United States Patent
Dally et al.

(10) Patent No.: US 9,156,824 B2
(45) Date of Patent: Oct. 13, 2015

(54) CDC7 INHIBITORS

(71) Applicant: Eli Lilly and Company, Indianapolis, IN (US)

(72) Inventors: Robert Dean Dally, Carmel, IN (US); Timothy Andrew Woods, Edinburgh, IN (US)

(73) Assignee: Eli Lilly and Company, Indianapolis (IN)

( * ) Notice: Subject to any disclaimer, the term of this patent is extended or adjusted under 35 U.S.C. 154(b) by 0 days.

(21) Appl. No.: 14/200,141

(22) Filed: Mar. 7, 2014

(65) Prior Publication Data

US 2014/0275121 A1  Sep. 18, 2014

Related U.S. Application Data

(60) Provisional application No. 61/789,108, filed on Mar. 15, 2013, provisional application No. 61/782,798, filed on Mar. 14, 2013.

(51) Int. Cl.
| | |
|---|---|
| *C07D 401/12* | (2006.01) |
| *C07D 239/42* | (2006.01) |
| *C07D 403/14* | (2006.01) |

(52) U.S. Cl.
CPC .................................. *C07D 403/14* (2013.01)

(58) Field of Classification Search
None
See application file for complete search history.

(56) References Cited

U.S. PATENT DOCUMENTS

2009/0203690 A1   8/2009   Akritopoulou-Zanze et al.

FOREIGN PATENT DOCUMENTS

| WO | 2005/100351 | | 10/2005 |
|---|---|---|---|
| WO | 2006/136606 | A2 | 12/2006 |
| WO | 2008/060789 | A2 | 5/2008 |

OTHER PUBLICATIONS

Simone, Oncology: Introduction, Cecil Textbook of Medicine, 20th Edition, 1996 vol. 1, pp. 1004-1010.*

* cited by examiner

*Primary Examiner* — Sang-Ming Hui
*Assistant Examiner* — Andrew Lee
(74) *Attorney, Agent, or Firm* — Danica Hostettler

(57) ABSTRACT

The present invention provides isoindolinone compounds, or a pharmaceutically acceptable salt thereof, that inhibit CDC7 and, therefore may be useful in treating cancer.

32 Claims, No Drawings

CDC7 INHIBITORS

The present invention relates to isoindolinone compounds, or pharmaceutically acceptable salts thereof, that inhibit CDC7 and may be useful for treating cancer.

CDC7 is a serine/threonine kinase that plays a key role in the initiation of DNA replication and regulation of the S phase cell cycle check point. Upregulation of CDC7 has been observed in numerous tumor cell lines. Also, inhibition of CDC7 in such cell lines has resulted in cell cycle arrest. Therefore, CDC7 inhibition may be useful for cancer therapy.

CDC7 inhibitors are known in the art. Isoindolinone compounds are also known in the art. WO 2005/100351 discloses certain isoindolinone compounds as nicotinic acetylcholine receptor-reactive compounds.

There remains a need to provide alternative CDC7 inhibitors for treatment of cancer. Accordingly, the present invention provides inhibitors of CDC7 which may be useful for treating cancer.

The present invention provides a compound which is 3-(5-fluoropyrimidin-4-yl)-3-methyl-6-(1H-pyrazol-4-yl)isoindolin-1-one, or a pharmaceutically acceptable salt thereof.

The present invention provides a compound which is 3-(5-fluoropyrimidin-4-yl)-3-methyl-6-(1H-pyrazol-4-yl)isoindolin-1-one, isomer 2, or a pharmaceutically acceptable salt thereof.

The present invention provides a compound which is 3-(5-fluoropyrimidin-4-yl)-3-methyl-6-(1H-pyrazol-4-yl)isoindolin-1-one, isomer 1, or a pharmaceutically acceptable salt thereof.

As a particular embodiment, the present invention provides the compound which is 3-(5-fluoropyrimidin-4-yl)-3-methyl-6-(1H-pyrazol-4-yl)isoindolin-1-one. As another particular embodiment, the present invention provides the compound which is 3-(5-fluoropyrimidin-4-yl)-3-methyl-6-(1H-pyrazol-4-yl)isoindolin-1-one, isomer 2. As an additional particular embodiment, the present invention provides the compound which is 3-(5-fluoropyrimidin-4-yl)-3-methyl-6-(1H-pyrazol-4-yl)isoindolin-1-one, isomer 1.

The present invention provides a pharmaceutical composition comprising 3-(5-fluoropyrimidin-4-yl)-3-methyl-6-(1H-pyrazol-4-yl)isoindolin-1-one, or a pharmaceutically acceptable salt thereof, and a pharmaceutically acceptable carrier, diluent, or excipient. The present invention provides a pharmaceutical composition comprising 3-(5-fluoropyrimidin-4-yl)-3-methyl-6-(1H-pyrazol-4-yl)isoindolin-1-one, and a pharmaceutically acceptable carrier, diluent, or excipient. The present invention also provides a pharmaceutical composition comprising 3-(5-fluoropyrimidin-4-yl)-3-methyl-6-(1H-pyrazol-4-yl)isoindolin-1-one, isomer 2, or a pharmaceutically acceptable salt thereof, and a pharmaceutically acceptable carrier, diluent, or excipient. The present invention additionally provides a pharmaceutical composition comprising 3-(5-fluoropyrimidin-4-yl)-3-methyl-6-(1H-pyrazol-4-yl)isoindolin-1-one, isomer 2, and a pharmaceutically acceptable carrier, diluent, or excipient. The present invention also provides a pharmaceutical composition comprising 3-(5-fluoropyrimidin-4-yl)-3-methyl-6-(1H-pyrazol-4-yl)isoindolin-1-one, isomer 1, or a pharmaceutically acceptable salt thereof, and a pharmaceutically acceptable carrier, diluent, or excipient. The present invention additionally provides a pharmaceutical composition comprising 3-(5-fluoropyrimidin-4-yl)-3-methyl-6-(1H-pyrazol-4-yl)isoindolin-1-one, isomer 1, and a pharmaceutically acceptable carrier, diluent, or excipient.

The present invention provides a method for treating cancer comprising administering to a patient in need thereof an effective amount of 3-(5-fluoropyrimidin-4-yl)-3-methyl-6-(1H-pyrazol-4-yl)isoindolin-1-one, or a pharmaceutically acceptable salt thereof. The present invention provides a method for treating cancer comprising administering to a patient in need thereof an effective amount of 3-(5-fluoropyrimidin-4-yl)-3-methyl-6-(1H-pyrazol-4-yl)isoindolin-1-one. The present invention also provides a method for treating cancer comprising administering to a patient in need thereof an effective amount of 3-(5-fluoropyrimidin-4-yl)-3-methyl-6-(1H-pyrazol-4-yl)isoindolin-1-one, isomer 2, or a pharmaceutically acceptable salt thereof. The present invention additionally provides a method for treating cancer comprising administering to a patient in need thereof an effective amount of 3-(5-fluoropyrimidin-4-yl)-3-methyl-6-(1H-pyrazol-4-yl)isoindolin-1-one, isomer 2. The present invention also provides a method for treating cancer comprising administering to a patient in need thereof an effective amount of 3-(5-fluoropyrimidin-4-yl)-3-methyl-6-(1H-pyrazol-4-yl)isoindolin-1-one, isomer 1, or a pharmaceutically acceptable salt thereof. The present invention additionally provides a method for treating cancer comprising administering to a patient in need thereof an effective amount of 3-(5-fluoropyrimidin-4-yl)-3-methyl-6-(1H-pyrazol-4-yl)isoindolin-1-one, isomer 1.

The present invention provides 3-(5-fluoropyrimidin-4-yl)-3-methyl-6-(1H-pyrazol-4-yl)isoindolin-1-one, or a pharmaceutically acceptable salt thereof, for use in therapy. The present invention provides 3-(5-fluoropyrimidin-4-yl)-3-methyl-6-(1H-pyrazol-4-yl)isoindolin-1-one, or a pharmaceutically acceptable salt thereof, for use in the treatment of cancer. The present invention provides a pharmaceutical composition for use in treating cancer, the pharmaceutical composition comprising 3-(5-fluoropyrimidin-4-yl)-3-methyl-6-(1H-pyrazol-4-yl)isoindolin-1-one, or a pharmaceutically acceptable salt thereof.

The present invention provides 3-(5-fluoropyrimidin-4-yl)-3-methyl-6-(1H-pyrazol-4-yl)isoindolin-1-one for use in therapy. The present invention provides 3-(5-fluoropyrimidin-4-yl)-3-methyl-6-(1H-pyrazol-4-yl)isoindolin-1-one for use in the treatment of cancer. The present invention provides a pharmaceutical composition for use in treating cancer, the pharmaceutical composition comprising 3-(5-fluoropyrimidin-4-yl)-3-methyl-6-(1H-pyrazol-4-yl)isoindolin-1-one.

The present invention provides 3-(5-fluoropyrimidin-4-yl)-3-methyl-6-(1H-pyrazol-4-yl)isoindolin-1-one, isomer 2, or a pharmaceutically acceptable salt thereof, for use in therapy. The present invention provides 3-(5-fluoropyrimidin-4-yl)-3-methyl-6-(1H-pyrazol-4-yl)isoindolin-1-one, isomer 2, or a pharmaceutically acceptable salt thereof, for use in the treatment of cancer. The present invention provides a pharmaceutical composition for use in treating cancer, the pharmaceutical composition comprising 3-(5-fluoropyrimidin-4-yl)-3-methyl-6-(1H-pyrazol-4-yl)isoindolin-1-one, isomer 2, or a pharmaceutically acceptable salt thereof.

The present invention provides 3-(5-fluoropyrimidin-4-yl)-3-methyl-6-(1H-pyrazol-4-yl)isoindolin-1-one, isomer 2 for use in therapy. The present invention provides 3-(5-fluoropyrimidin-4-yl)-3-methyl-6-(1H-pyrazol-4-yl)isoindolin-1-one, isomer 2 for use in the treatment of cancer. The present invention provides a pharmaceutical composition for use in treating cancer, the pharmaceutical composition comprising 3-(5-fluoropyrimidin-4-yl)-3-methyl-6-(1H-pyrazol-4-yl)isoindolin-1-one, isomer 2.

The present invention provides 3-(5-fluoropyrimidin-4-yl)-3-methyl-6-(1H-pyrazol-4-yl)isoindolin-1-one, isomer 1, or a pharmaceutically acceptable salt thereof, for use in therapy. The present invention provides 3-(5-fluoropyrimidin-4-yl)-3-methyl-6-(1H-pyrazol-4-yl)isoindolin-1-one, isomer 1, or a pharmaceutically acceptable salt thereof, for use in the treatment of cancer. The present invention provides a pharmaceutical composition for use in treating cancer, the pharmaceutical composition comprising 3-(5-fluoropyrimidin-4-yl)-3-methyl-6-(1H-pyrazol-4-yl)isoindolin-1-one, isomer 1, or a pharmaceutically acceptable salt thereof.

The present invention provides 3-(5-fluoropyrimidin-4-yl)-3-methyl-6-(1H-pyrazol-4-yl)isoindolin-1-one, isomer 1 for use in therapy. The present invention provides 3-(5-fluoropyrimidin-4-yl)-3-methyl-6-(1H-pyrazol-4-yl)isoindolin-1-one, isomer 1 for use in the treatment of cancer. The present invention provides a pharmaceutical composition for use in treating cancer, the pharmaceutical composition comprising 3-(5-fluoropyrimidin-4-yl)-3-methyl-6-(1H-pyrazol-4-yl) isoindolin-1-one, isomer 1.

The present invention provides the use of 3-(5-fluoropyrimidin-4-yl)-3-methyl-6-(1H-pyrazol-4-yl)isoindolin-1-one, or a pharmaceutically acceptable salt thereof, in the manufacture of a medicament for the treatment of cancer. The present invention also provides the use of 3-(5-fluoropyrimidin-4-yl)-3-methyl-6-(1H-pyrazol-4-yl)isoindolin-1-one in the manufacture of a medicament for the treatment of cancer.

The present invention provides the use of 3-(5-fluoropyrimidin-4-yl)-3-methyl-6-(1H-pyrazol-4-yl)isoindolin-1-one, isomer 2, or a pharmaceutically acceptable salt thereof, in the manufacture of a medicament for the treatment of cancer. The present invention also provides the use of 3-(5-fluoropyrimidin-4-yl)-3-methyl-6-(1H-pyrazol-4-yl)isoindolin-1-one, isomer 2 in the manufacture of a medicament for the treatment of cancer.

The present invention provides the use of 3-(5-fluoropyrimidin-4-yl)-3-methyl-6-(1H-pyrazol-4-yl)isoindolin-1-one, isomer 1, or a pharmaceutically acceptable salt thereof, in the manufacture of a medicament for the treatment of cancer. The present invention also provides the use of 3-(5-fluoropyrimidin-4-yl)-3-methyl-6-(1H-pyrazol-4-yl)isoindolin-1-one, isomer 1 in the manufacture of a medicament for the treatment of cancer.

The present invention provides 3-(5-fluoropyrimidin-4-yl)-3-methyl-6-(1H-pyrazol-4-yl)isoindolin-1-one, isomer 2, hydrate in a crystalline form. The present invention also provides 3-(5-fluoropyrimidin-4-yl)-3-methyl-6-(1H-pyrazol-4-yl)isoindolin-1-one, isomer 2, hydrate in a crystalline form characterized by a X-ray powder diffraction pattern having characteristic peaks, in 2θ±0.2, occurring at 22.27 and one or more of 13.46, 16.54, 16.66, 18.10 and 23.13.

The present invention provides a compound which is 3-(5-fluoropyrimidin-4-yl)-3-methyl-6-(1H-pyrazol-4-yl)isoindolin-1-one, isomer 2, or a pharmaceutically acceptable salt thereof, which is alternatively identified as (3R)-3-(5-fluoropyrimidin-4-yl)-3-methyl-6-(1H-pyrazol-4-yl)isoindolin-1-one, or a pharmaceutically acceptable salt thereof.

The present invention provides a compound which is 3-(5-fluoropyrimidin-4-yl)-3-methyl-6-(1H-pyrazol-4-yl)isoindolin-1-one, isomer 1, or a pharmaceutically acceptable salt thereof, which is alternatively identified as (3S)-3-(5-fluoropyrimidin-4-yl)-3-methyl-6-(1H-pyrazol-4-yl)isoindolin-1-one, or a pharmaceutically acceptable salt thereof.

As a particular embodiment, the present invention provides the compound which is (3R)-3-(5-fluoropyrimidin-4-yl)-3-methyl-6-(1H-pyrazol-4-yl)isoindolin-1-one. As an additional particular embodiment, the present invention provides the compound which is (3S)-3-(5-fluoropyrimidin-4-yl)-3-methyl-6-(1H-pyrazol-4-yl)isoindolin-1-one.

The present invention also provides a pharmaceutical composition comprising (3R)-3-(5-fluoropyrimidin-4-yl)-3-methyl-6-(1H-pyrazol-4-yl)isoindolin-1-one, or a pharmaceutically acceptable salt thereof, and a pharmaceutically acceptable carrier, diluent, or excipient. The present invention additionally provides a pharmaceutical composition comprising (3R)-3-(5-fluoropyrimidin-4-yl)-3-methyl-6-(1H-pyrazol-4-yl)isoindolin-1-one, and a pharmaceutically acceptable carrier, diluent, or excipient. The present invention also provides a pharmaceutical composition comprising (3S)-3-(5-fluoropyrimidin-4-yl)-3-methyl-6-(1H-pyrazol-4-yl) isoindolin-1-one, or a pharmaceutically acceptable salt thereof, and a pharmaceutically acceptable carrier, diluent, or excipient. The present invention additionally provides a pharmaceutical composition comprising (3S)-3-(5-fluoropyrimidin-4-yl)-3-methyl-6-(1H-pyrazol-4-yl)isoindolin-1-one, and a pharmaceutically acceptable carrier, diluent, or excipient.

The present invention provides (3R)-3-(5-fluoropyrimidin-4-yl)-3-methyl-6-(1H-pyrazol-4-yl)isoindolin-1-one, or a pharmaceutically acceptable salt thereof, for use in therapy. The present invention provides (3R)-3-(5-fluoropyrimidin-4-yl)-3-methyl-6-(1H-pyrazol-4-yl)isoindolin-1-one, or a pharmaceutically acceptable salt thereof, for use in the treatment of cancer. The present invention provides a pharmaceutical composition for use in treating cancer, the pharmaceutical composition comprising (3R)-3-(5-fluoropyrimidin-4-yl)-3-methyl-6-(1H-pyrazol-4-yl)isoindolin-1-one, or a pharmaceutically acceptable salt thereof.

The present invention provides (3R)-3-(5-fluoropyrimidin-4-yl)-3-methyl-6-(1H-pyrazol-4-yl)isoindolin-1-one for use in therapy. The present invention provides (3R)-3-(5-fluoropyrimidin-4-yl)-3-methyl-6-(1H-pyrazol-4-yl)isoindolin-1-one for use in the treatment of cancer. The present invention provides a pharmaceutical composition for use in treating cancer, the pharmaceutical composition comprising (3R)-3-(5-fluoropyrimidin-4-yl)-3-methyl-6-(1H-pyrazol-4-yl)isoindolin-1-one.

The present invention provides (3S)-3-(5-fluoropyrimidin-4-yl)-3-methyl-6-(1H-pyrazol-4-yl)isoindolin-1-one, or a pharmaceutically acceptable salt thereof, for use in therapy. The present invention provides (3S)-3-(5-fluoropyrimidin-4-yl)-3-methyl-6-(1H-pyrazol-4-yl)isoindolin-1-one, or a pharmaceutically acceptable salt thereof, for use in the treatment of cancer. The present invention provides a pharmaceutical composition for use in treating cancer, the pharmaceutical composition comprising (3S)-3-(5-fluoropyrimidin-4-yl)-3-methyl-6-(1H-pyrazol-4-yl)isoindolin-1-one, or a pharmaceutically acceptable salt thereof.

The present invention provides (3S)-3-(5-fluoropyrimidin-4-yl)-3-methyl-6-(1H-pyrazol-4-yl)isoindolin-1-one for use in therapy. The present invention provides (3S)-3-(5-fluoropyrimidin-4-yl)-3-methyl-6-(1H-pyrazol-4-yl)isoindolin-1-one for use in the treatment of cancer. The present invention provides a pharmaceutical composition for use in treating cancer, the pharmaceutical composition comprising (3S)-3-(5-fluoropyrimidin-4-yl)-3-methyl-6-(1H-pyrazol-4-yl) isoindolin-1-one.

The present invention provides the use of (3R)-3-(5-fluoropyrimidin-4-yl)-3-methyl-6-(1H-pyrazol-4-yl)isoindolin-1-one, or a pharmaceutically acceptable salt thereof, in the manufacture of a medicament for the treatment of cancer. The present invention also provides the use of (3R)-3-(5-fluoropyrimidin-4-yl)-3-methyl-6-(1H-pyrazol-4-yl)isoindolin-1-one in the manufacture of a medicament for the treatment of cancer.

The present invention provides the use of (3S)-3-(5-fluoropyrimidin-4-yl)-3-methyl-6-(1H-pyrazol-4-yl)isoindolin-1-one, or a pharmaceutically acceptable salt thereof, in the manufacture of a medicament for the treatment of cancer. The present invention also provides the use of (3S)-3-(5-fluoropyrimidin-4-yl)-3-methyl-6-(1H-pyrazol-4-yl)isoindolin-1-one in the manufacture of a medicament for the treatment of cancer.

The present invention provides (3R)-3-(5-fluoropyrimidin-4-yl)-3-methyl-6-(1H-pyrazol-4-yl)isoindolin-1-one, hydrate in a crystalline form. The present invention also provides (3R)-3-(5-fluoropyrimidin-4-yl)-3-methyl-6-(1H-pyrazol-4-yl)isoindolin-1-one, hydrate in a crystalline form characterized by a X-ray powder diffraction pattern having characteristic peaks, in 2θ±0.2, occurring at 22.27 and one or more of 13.46, 16.54, 16.66, 18.10 and 23.13.

Furthermore, the present invention provides preferred embodiments of the methods and uses as described herein, in which cancer is selected from the group consisting of breast cancer, triple negative breast cancer, ovarian cancer, lung cancer, colorectal cancer, hematologic cancer, and leukemia.

As used above, and throughout the description of the invention, the following terms, unless otherwise indicated, shall be understood to have the following meanings:

A "pharmaceutically acceptable carrier, diluent, or excipient" is a medium generally accepted in the art for the delivery of biologically active agents to mammals, e.g., humans.

"Pharmaceutically acceptable salts" refers to the relatively non-toxic, inorganic and organic salts of compounds of the present invention.

"Effective amount" means the amount of the compound, or pharmaceutically acceptable salt thereof, of the present invention or pharmaceutical composition containing a compound, or pharmaceutically acceptable salt thereof, of the present invention that will elicit the biological or medical response of or desired therapeutic effect on a tissue, system, animal, mammal or human that is being sought by the researcher, veterinarian, medical doctor or other clinician.

The terms "treatment," "treat," "treating," and the like, are meant to include slowing or reversing the progression of a disorder. These terms also include alleviating, ameliorating, attenuating, eliminating, or reducing one or more symptoms of a disorder or condition, even if the disorder or condition is not actually eliminated and even if progression of the disorder or condition is not itself slowed or reversed.

The compounds of the present invention are capable of reaction, for example, with a number of inorganic and organic acids to form pharmaceutically acceptable salts. Such pharmaceutically acceptable salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol 66, No. 1, January 1977.

The compounds of the present invention are preferably formulated as pharmaceutical compositions using a pharmaceutically acceptable carrier, diluent, or excipient and administered by a variety of routes. Preferably, such compositions are for oral administration. Such pharmaceutical compositions and processes for preparing them are well known in the art. See, e.g., Remington: The Science and Practice of Pharmacy (A. Gennaro, et al., eds., 21st ed., Mack Publishing Co., 2005).

The amount of the compound of the present invention actually administered will be determined by a physician under the relevant circumstances, including the condition to be treated, the chosen route of administration, the actual compound or compounds of the present invention administered, the age, weight, and response of the individual patient, and the severity of the patient's symptoms. Dosages per day normally fall within the range of about 1 to about 1000 mg. In some instances, dosage levels below the lower limit of the aforesaid range may be more than adequate, while in other cases still larger doses may be employed. Dosage levels can be determined by one of skill in the art.

The compounds of the present invention, or pharmaceutically acceptable salts thereof, may be prepared by a variety of procedures known in the art, as well as those described in the Preparations and Examples below. The specific synthetic steps for each of the routes described may be combined in different ways to prepare the compounds of the invention, or pharmaceutically acceptable salts thereof.

The reagents and starting materials are generally readily available to one of ordinary skill in the art. Others may be made by standard techniques of organic and heterocyclic chemistry, techniques which are known to one of ordinary skill in the art, and the procedures described in the Examples which follow including any novel procedures. The following Preparations and Examples further illustrate the invention. The compounds illustrated herein are named and numbered using Symyx Draw Version 3.2, Symyx Draw Version 4.0, or IUPACNAME ACDLABS.

Individual isomers, enantiomers, or diastereomers may be separated or resolved by one of ordinary skill in the art at any convenient point in the synthesis of compounds by methods such as selective crystallization techniques or chiral chromatography (See, e.g., Enantiomers, Racemates, and Resolutions (J. Jacques, et al., John Wiley and Sons, Inc., 1981)). The designation "Isomer 1" refers to the compound that elutes from chiral chromatography first. The designation "Isomer 2" refers to the compound that elutes from chiral chromatography second.

As used herein, the following terms have the meanings indicated: "ADP" refers to adenosine diphosphate; "ATP" refers to adenosine triphosphate; "Balb/c" refers to albino; "BCA" refers to bicinchoninic acid; "DMSO" refers to dimethyl sulfoxide; "DTT" refers to dithiothreitol; "EDTA" refers to ethylenediaminetetraacetic acid; "ee" refers to enantiomeric excess; "Ex" refers to example; "FBS" refers to Fetal Bovine Serum; "FP" refers to fluorescence polarization; "GAPDH" refers to glyceraldehyde 3-phosphate dehydrogenase; "HEC" refers to hydroxy ethyl cellulose; "HEPES" refers to 4-(2-hydroxyethyl)-1-piperazineethanesulfonic acid; "hr" refers to hour or hours; "$IC_{50}$" refers to the concentration of an agent that produces 50% of the maximal inhibitory response possible for that agent; "IVTI" refers to in vivo target inhibition; "MCM2 refers to minichromosome maintenance protein; "min" refers to minute or minutes; "PBS" refers to phosphate buffered saline; "P.O." refers to oral administration; "Prep" refers to preparation; "PVDF" refers to polyvinylidine difluoride; "RPMI" refers to Roswell Park Memorial Institute; "RNase" refers to ribonuclease; "RuPhos" refers to 2-dicyclohexylphosphino-2',6'-diisopropoxybiphenyl; "$R_t$" refer to retention time; "SDS-Page" refers to sodium dodecyl sulfate polyacrylamide gel electrophoresis; "SCX" refers to strong cation exchange; "SFC" refers to supercritical fluid chromatography; and "THF" refers to tetrahydrofuran.

Preparation 1

Methyl 5-bromo-2-iodobenzoate

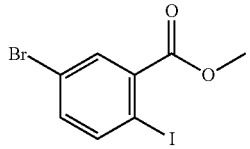

Add 5-bromo-2-iodobenzoic acid (1998 g, 6.11 mol) portion wise to a 20° C. solution of sulfuric acid (100 mL) in methanol (13 L). Heat the suspension to reflux for 24 hours, then cool to 20° C. and remove the solvent under reduced pressure. Pour the residue into a 1:1 mixture of methyl-tert-butyl ether and ice water (20 L) and separate the phases. Extract the aqueous phase with methyl-tert-butyl ether (1.5 L), combine the organic phases and wash with aqueous 0.2 M NaOH (5 L), wash with saturated aqueous sodium chloride, dry over sodium sulfate, filter, and evaporate under reduced pressure. Dissolve the crude product in 40-45° C. petroleum ether (10 L), filter through a pad of diatomaceous earth and evaporate under reduced pressure. Dissolve the residue in petroleum ether (5 L) and cool to −50° C., filter the first crop solids, wash the solid with ice cold petroleum ether. Evaporate the mother liquor, redissolve the solid in petroleum ether (1 L), cool to −50° C., and filter a second crop. Combine first and second crops and dry in open air to provide the title compound as a yellow solid (1880 g, 90%).

Preparation 2

Methyl 5-bromo-2-ethylbenzoate

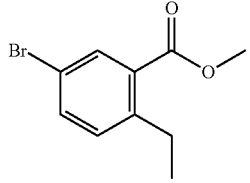

Add diethyl zinc (3050 mL, 3.05 mol, 1 M hexane) over 3 hours to a 5° C. solution of methyl 5-bromo-2-iodobenzoate (1876 g, 5.50 mol) and (1,1'-bis(diphenylphosphino)ferrocene)palladium(II) chloride (40 g, 0.05 mol). Heat the mixture to 60-65° C. over 2 hours and stir for an additional 2 hours, then cool to 10-15° C. and pour into ice cold aqueous 1 M HCl (10 L). Separate the phases, extract the aqueous layer with methyl-tert-butyl ether (2×10 L), combine the organic phases, wash with saturated aqueous sodium chloride, dry over sodium sulfate, filter, and evaporate under reduced pressure. Dissolve in ethyl acetate (400 mL) and add petroleum ether (8 L), then let stand at 15-20° C. for 16 hours and filter through a pad of silica gel, wash with ethyl acetate/petroleum ether (1:20, 8 L) and evaporate the filtrate under reduced pressure to provide the title compound as a pale yellow oil (1306 g, 96%). ES/MS m/e: ($^{79}$Br/$^{81}$Br) 243/245 (M+H).

Preparation 3

Methyl 5-bromo-2-(1-bromoethyl)benzoate

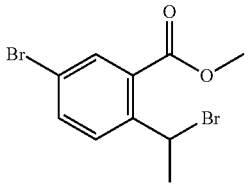

Add N-bromosuccinimide (1090 g, 6.12 mol) and 2,2'-azo-bis-isobutyronitrile (11.4 g, 0.069 mol) to a 20° C. solution of methyl 5-bromo-2-ethylbenzoate (1296 g, 5.33 mol) in carbon tetrachloride (7 L). Heat to reflux for 4 hours, cool to 20-30° C. and wash with water (10 L), extract the aqueous phase with dichloromethane (5 L), combine the organic layers, and wash with water (10 L), Na$_2$SO$_3$ (5 L) and saturated aqueous sodium chloride. Dry with sodium sulfate, filter, and evaporate under reduced pressure to give the title compound as a pale yellow solid (1791 g, 104% crude). ES/MS m/z: 241 (M−HBr).

Preparation 4

6-Bromo-2-[(1R)-1-(4-methoxyphenyl)ethyl]-3-methyl-isoindolin-1-one

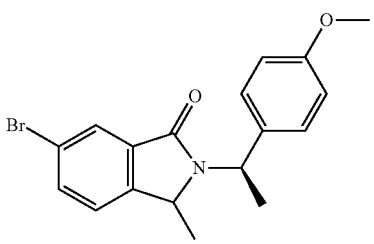 [SMILES: COc1ccc([C@@H](C)N2C(=O)c3cc(Br)ccc3C2C)cc1]

Add solid methyl 5-bromo-2-(1-bromoethyl)benzoate (1724 g, 5.35 mol) to a solution of commercially available (R)-1-(4-methoxyphenyl)ethanamine (BePharm, WZG111219-071; 974 g, 6.44 mol) and triethylamine (1710 mL, 12.26 mol) in methanol (12 L). Heat the mixture for 10 hours at 67° C. then evaporate to dryness under reduced pressure. Partition the residue with ethyl acetate (5 L) and aqueous 1 N HCl (10 L), separate the phases, wash the organic phase again with aqueous 1 N HCl (5 L), saturated sodium bicarbonate, saturated aqueous sodium chloride, then dry over sodium sulfate, filter, and evaporate under reduced pressure. Dissolve the dark red oil in methyl-tert-butyl ether (750 mL) and add petroleum ether (3 L) with vigorous stirring. Filter the solids, wash with methyl-tert-butyl ether/petroleum ether (1:8), petroleum ether, dry in open air to give the title compound as an off-white solid (1014 g, 52%). ES/MS m/z: 360 (M+H).

Preparation 5

2-[(1R)-1-(4-Methoxyphenyl)ethyl]-3-methyl-6-(1-tetrahydropyran-2-ylpyrazol-4-yl)isoindolin-1-one

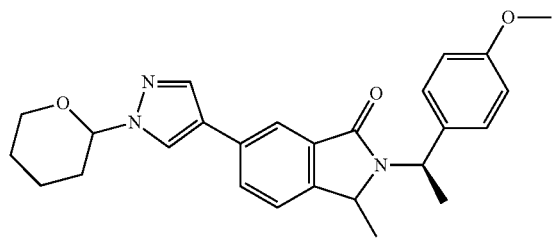 [SMILES: COc1ccc([C@@H](C)N2C(=O)c3cc(-c4cnn(C5CCCCO5)c4)ccc3C2C)cc1]

Combine 6-bromo-2-[(1R)-1-(4-methoxyphenyl)ethyl]-3-methyl-isoindolin-1-one (64 g, 177 mmol), 1-(tetrahydro-2H-pyran-2-yl)-4-(4,4,5,5-tetramethyl-1,3,2-dioxaborolan-2-yl)-1H-pyrazole (67 g, 295 mmol), potassium carbonate (70 g, 506 mmol), (1,1'-bis(diphenylphosphino)ferrocene)palladium(II) chloride (9 g, 11 mmol), dioxane (800 mL), and water (212 mL) under nitrogen and heat to 70-75° C. for 16 hours. Add 1-(tetrahydro-2H-pyran-2-yl)-4-(4,4,5,5-tetramethyl-1,3,2-dioxaborolan-2-yl)-1H-pyrazole (15 g, 54 mmol) and heat to 80-85° C. for 2 hours. Concentrate under reduced pressure to 200 mL, add ethyl acetate (500 mL) and water (500 mL), stir for 30 minutes, and filter the solids. Combine the solids and the organic layer and evaporate under reduced pressure. Dissolve the residue in dichloromethane and filter through a pad of silica gel. Wash the silica gel pad with dichloromethane/ethyl acetate (1:0) and then (2:1) and evaporate to dryness under reduced pressure. Slurry the solid in a 2:1 mixture of petroleum ether/ethyl acetate (600 mL) for 30 minutes at 25-30° C. and filter to collect the solid to give the title compound as an off-white solid (68 g, 89%). ES/MS m/z: 432 (M+H).

Preparation 6

3-(6-Chloro-5-fluoro-pyrimidin-4-yl)-2-[(1R)-1-(4-methoxyphenyl)ethyl]-3-methyl-6-(1-tetrahydropyran-2-ylpyrazol-4-yl)isoindolin-1-one

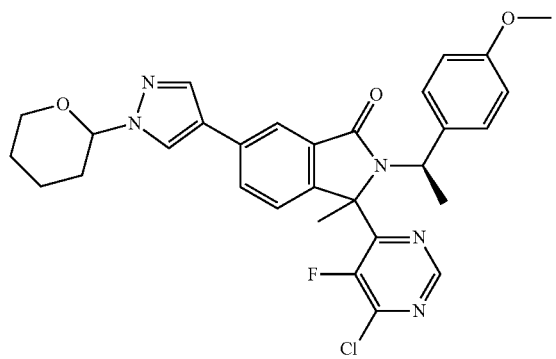 [SMILES: COc1ccc([C@@H](C)N2C(=O)c3cc(-c4cnn(C5CCCCO5)c4)ccc3C2(C)c2ncnc(Cl)c2F)cc1]

Add sodium bis(trimethylsilyl)amide (210 mL, 210 mmol, 1 M THF) drop wise over 60 minutes to an ice cold suspension of 2-[(1R)-1-(4-methoxyphenyl)ethyl]-3-methyl-6-(1-tetrahydropyran-2-ylpyrazol-4-yl)isoindolin-1-one (62 g, 144 mmol) and 4,6-dichloro-5-fluoropyrimidine (31 g, 186 mmol) in tetrahydrofuran (620 mL). Stir the solution 60 minutes at 0° C. and then dilute the mixture with ethyl acetate (1 L) and water (1 L). Wash the organic phase with saturated aqueous sodium chloride and evaporate under reduced pressure. Dissolve the residue in 1:1 petroleum ether/ethyl acetate, filter through a pad of silica gel, and evaporate to give the title compound as a yellow foam (83 g, 103%). ES/MS m/z: 562 (M+H).

Preparation 7

3-(5-Fluoropyrimidin-4-yl)-2-[(1R)-1-(4-methoxyphenyl)ethyl]-3-methyl-6-(1-tetrahydropyran-2-ylpyrazol-4-yl)isoindolin-1-one

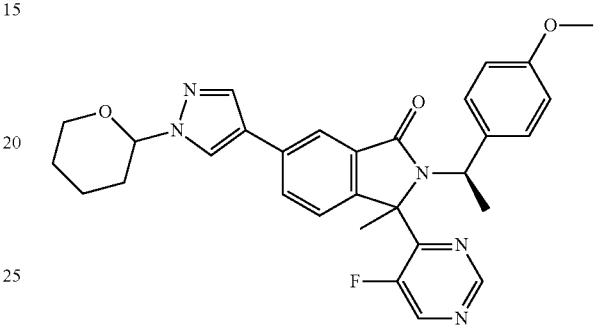

Add triethylamine (40 mL, 287 mmol) and 20% palladium hydroxide on carbon (14 g) to a solution of 3-(6-chloro-5-fluoro-pyrimidin-4-yl)-2-[(1R)-1-(4-methoxyphenyl)ethyl]-3-methyl-6-(1-tetrahydropyran-2-ylpyrazol-4-yl)isoindolin-1-one (80 g, 142 mmol) in ethyl acetate (2.1 L) and hydrogenate with hydrogen gas (30 psi) at 20-25° C. for 16 hours. Repeat reaction conditions with 5 grams 3-(6-chloro-5-fluoro-pyrimidin-4-yl)-2-[(1R)-1-(4-methoxyphenyl)ethyl]-3-methyl-6-(1-tetrahydropyran-2-ylpyrazol-4-yl)isoindolin-1-one. Combine both reactions and filter through diatomaceous earth and evaporate to give the title compound as a yellow foam (77 g, 102%). ES/MS m/z: 528 (M+H).

Preparation 8

6-Bromo-3-(5-fluoropyrimidin-4-yl)-2-[(1R)-1-(4-methoxyphenyl)ethyl]-3-methyl-isoindolin-1-one

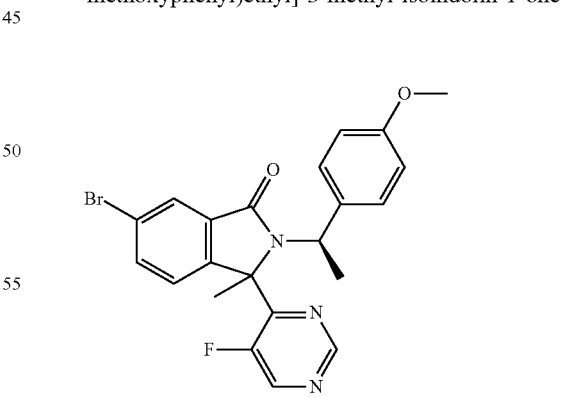

Dissolve 6-bromo-2-[(1R)-1-(4-methoxyphenyl)ethyl]-3-methyl-isoindolin-1-one (2.814 mmol, 1.014 g) in tetrahydrofuran (28 mL). Add 4-chloro-5-fluoro-pyrimidine (5.628 mmol, 518 µL) and cool to 0° C. Add potassium hexamethyldisilazide (4.502 mmol, 9 mL, 0.5 M in toluene) over 7 minutes and stir for 1 hour, then warm to ambient temperature and stir for 90 minutes. Pour into methyl-tert-butyl ether and aqueous 1 M HCl, add water and separate the layers. Wash with aqueous 1 N HCl, filter, wash with saturated aqueous sodium chloride, dry over magnesium sulfate, filter through a 2 cm pad of silica gel, and evaporate under reduced pressure to provide an oil. Purify on silica gel with 20-40% ethyl acetate/hexane to give the title compound as a foam (547 mg, 43%). ES/MS m/z: 456 (M+H).

EXAMPLE 1

3-(5-Fluoropyrimidin-4-yl)-3-methyl-6-(1H-pyrazol-4-yl)isoindolin-1-one

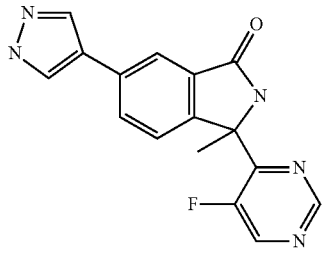 [SMILES: CC1(c2ncncc2F)NC(=O)c2cc(-c3cn[nH]c3)ccc21]

Dissolve 3-(5-fluoropyrimidin-4-yl)-2-[(1R)-1-(4-methoxyphenyl)ethyl]-3-methyl-6-(1-tetrahydropyran-2-ylpyrazol-4-yl)isoindolin-1-one (65 g, 123 mmol) in trifluoroacetic acid (600 mL) and heat to 75-80° C. for 16 hours. Evaporate under reduced pressure and dilute with ethyl acetate (500 mL) and water (500 mL). Adjust the pH of the aqueous layer to 8-9 with aqueous 6 N NaOH, extract the aqueous layer with ethyl acetate (3×500 mL), combine the organic layers, wash with saturated aqueous sodium chloride, dry with sodium sulfate, filter, and evaporate under reduced pressure. Chromatograph the crude product on silica gel with 50-100% ethyl acetate/petroleum ether. Combine the product fractions and evaporate under reduced pressure to give a yellow foam (33 g, 87% crude). Repeat the reaction conditions with 3-(5-fluoropyrimidin-4-yl)-2-[(1R)-1-(4-methoxyphenyl)ethyl]-3-methyl-6-(1-tetrahydropyran-2-ylpyrazol-4-yl)isoindolin-1-one and combine the products (10 g, 18.9 mmol). Dissolve the combined products in methanol and stir with SiliaBond® Thiol (Silia MetS® Thiol) at 15-20° C. for 20 hours, filter, and evaporate under reduced pressure to give the title compound with 77% ee (38 g, 87%).

EXAMPLE 2

3-(5-Fluoropyrimidin-4-yl)-3-methyl-6-(1H-pyrazol-4-yl)isoindolin-1-one, Isomer 2

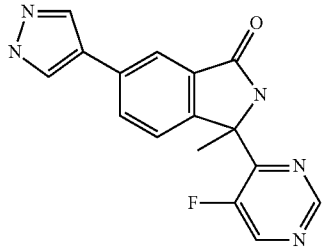 [SMILES: CC1(c2ncncc2F)NC(=O)c2cc(-c3cn[nH]c3)ccc21]

Separate the major enantiomer (Isomer 2) of 3-(5-fluoropyrimidin-4-yl)-3-methyl-6-(1H-pyrazol-4-yl)isoindolin-1-one (38 g, 123 mmol) from the minor enantiomer (Isomer 1) of 3-(5-fluoropyrimidin-4-yl)-3-methyl-6-(1H-pyrazol-4-yl)isoindolin-1-one by preparative chiral HPLC Supercritical fluid chromatography (SFC) (Column: Chiralpak OJ-H (5µ), 30×250 cm; eluent: 15% isopropanol in $CO_2$, flow 120 g/min at UV 214 nm). The second eluting isomer (Isomer 2) is the title compound (17 g, 45%, >98% ee). Chiral analysis (Column: Chiralpak OJ-H (5 µm) 4.6×250 mm, eluent: 20% isopropanol in $CO_2$, flow: 3 mL·min at UV 214 nm, $R_t$=5.78 minutes. ES/MS m/z: 310 (M+H).

EXAMPLE 3

3-(5-Fluoropyrimidin-4-yl)-3-methyl-6-(1H-pyrazol-4-yl)isoindolin-1-one

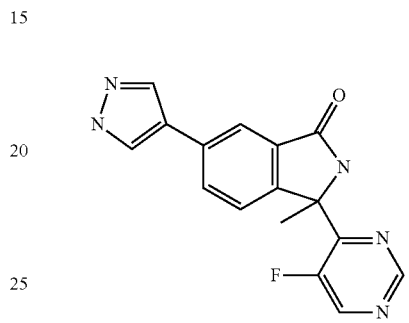

Combine RuPhos Palladium(II) phenethylamine chloride (60 µmol, 43 mg), dioxane (0.5 mL) and potassium tert-butoxide (1 M tetrahydrofuran, 60 µmol, 60 µL) under nitrogen, sonicate the mixture for 0.5 minute. Add the Ruphos catalyst mixture to a reaction vessel under nitrogen containing 6-bromo-3-(5-fluoropyrimidin-4-yl)-2-[(1R)-1-(4-methoxyphenyl)ethyl]-3-methyl-isoindolin-1-one (544 mg, 1.192 mmol), tert-butyl 4-(4,4,5,5-tetramethyl-1,3,2-dioxaborolan-2-yl)pyrazole-1-carboxylate (1.79 mmol, 526 mg), 1,4-dioxane (6 mL), sodium carbonate (3.6 mmol, 2.4 mL 1.5 M aqueous) and heat in a microwave at 150° C. for 30 minutes. Dilute the mixture with ethyl acetate, wash with aqueous 1.5 M sodium carbonate, wash with saturated aqueous sodium chloride, dry over magnesium sulfate, filter through diatomaceous earth, and evaporate to a light yellow residue. Dissolve the residue in anisole (1 mL) and trifluoroacetic acid (7 mL) and heat to 80° C. for 4 hours, then heat to 70° C. for 18 hours. Evaporate the mixture under reduced pressure, dissolve in methanol, load on a 10 g SCX column, wash with methanol (100 mL), elute with 2 M ammonia in methanol and evaporate. Purify on 40 g silica gel with a gradient of 1-8% methanol/dichloromethane to give the title compound as a white foam (279 mg, 76%). ES/MS m/z: 310 (M+H).

EXAMPLE 4

3-(5-Fluoropyrimidin-4-yl)-3-methyl-6-(1H-pyrazol-4-yl)isoindolin-1-one, Isomer 2, Hydrate

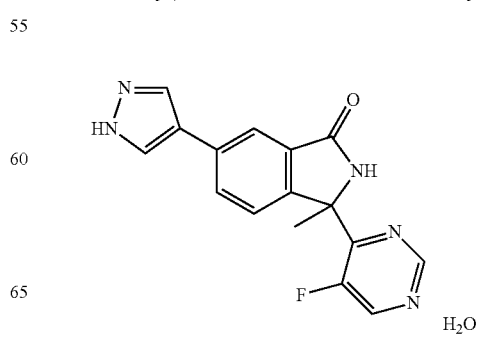

Suspend 3-(5-fluoropyrimidin-4-yl)-3-methyl-6-(1H-pyrazol-4-yl)isoindolin-1-one, isomer 2 (9.6 g, 0.03 mol) in 2% acetone in water (50 mL) and stir the mixture at 50° C. for 1.5 hours. Add acetone (1 mL) and heat the mixture to 65° C. for 1 hour before slowly cooling to room temperature over 12 hours. Filter the solids and rinse with four volumes of water. Dry the solid under vacuum at 50° C. for 6 hours to give the title compound (8.6 g, 90%).

X-Ray Powder Diffraction

The XRD patterns of crystalline solids are obtained on a Bruker D4 Endeavor X-ray powder diffractometer, equipped with a CuKa source (λ=1.54060 Å) and a Vantec detector, operating at 35 kV and 50 mA. The sample is scanned between 4 and 40° in 2θ, with a step size of 0.0087° in 2θ and a scan rate of 0.5 seconds/step, and with 0.6 mm divergence, 5.28 mm fixed anti-scatter, and 9.5 mm detector slits. The dry powder is packed on a quartz sample holder and a smooth surface is obtained using a glass slide. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction patterns, collected at ambient temperature and relative humidity, are adjusted based on NIST 675 standard peaks at 8.85 and 26.77 degrees 2-theta.

A prepared sample of Example 4 is characterized by an XRD pattern using CuKa radiation as having diffraction peaks (2-theta values) as described in Table 1 below. Specifically the pattern contains a peak at 22.27 in combination with one or more of the peaks selected from the group consisting of 13.46, 16.54, 16.66, 18.10 and 23.13 with a tolerance for the diffraction angles of 0.2 degrees.

TABLE 1

X-ray powder diffraction peaks of Example 4

| Peak | Angle (2-Theta°) | Intensity (%) |
|---|---|---|
| 1 | 7.16 | 14 |
| 2 | 13.46 | 51 |
| 3 | 14.82 | 19 |
| 4 | 16.54 | 32 |
| 5 | 16.66 | 32 |
| 6 | 16.96 | 14 |
| 7 | 18.10 | 27 |
| 8 | 18.84 | 15 |
| 9 | 19.33 | 15 |
| 10 | 21.78 | 15 |
| 11 | 22.27 | 100 |
| 12 | 23.13 | 30 |
| 13 | 23.51 | 15 |
| 14 | 23.86 | 13 |
| 15 | 25.99 | 18 |
| 16 | 27.21 | 14 |

EXAMPLE 5

(3R)-3-(5-Fluoropyrimidin-4-yl)-3-methyl-6-(1H-pyrazol-4-yl)isoindolin-1-one, dihydrochloride, acetonitrile solvate

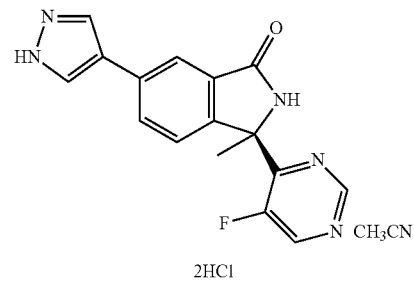

Add 0.25 M HCl (1 mL) to 3-(5-fluoropyrimidin-4-yl)-3-methyl-6-(1H-pyrazol-4-yl)isoindolin-1-one (Example 3, 0.084 mg, 0.27 mmol) and sonicate the sample. All the material is soluble. Evaporate the mixture to dryness, resulting in an oily residue. Add acetonitrile (2 mL) and the solution becomes yellow and crystals begin to form. Single crystals are isolated for single crystal X-ray diffraction. The sample is determined to be an acetonitrile solvate of a dihydrochloride salt. The chlorine atoms provide sufficient anomalous scattering to allow for the absolute stereochemistry of the molecule to be determined by single crystal X-ray diffraction.

A clear colorless prism-like specimen of $C_{18}H_{17}Cl_2FN_6O$, approximate dimensions 0.180 mm×0.200 mm×0.220 mm, is used for the X-ray crystallographic analysis. A total of 3318 frames are collected. The total exposure time is 1.84 hours. The frames are integrated with the Bruker SAINT software package using a narrow-frame algorithm. The integration of the data using an orthorhombic unit cell yielded a total of 13411 reflections to a maximum θ angle of 66.30° (0.84 Å resolution), of which 3304 are independent (average redundancy 4.059, completeness=97.8%, $R_{int}$=7.25%, $R_{sig}$=6.30%) and 2885 (87.32%) were greater than 2σ($F^2$). The final cell constants of a=8.0583(2) Å, b=36.3803(9) Å, c=6.96840(10) Å, volume=2042.88(8) Å³, are based upon the refinement of the XYZ-centroids of 6295 reflections above 20 σ(I) with 11.24°<2θ<132.0°. Data are corrected for absorption effects using the multi-scan method (SADABS). The ratio of minimum to maximum apparent transmission is 0.761. The calculated minimum and maximum transmission coefficients (based on crystal size) are 0.5466 and 0.6033.

The structure is solved and refined using the Bruker SHELXTL™ Software Package, using the space group P 21 21 2, with Z=4 for the formula unit, $C_{18}H_{17}Cl_2FN_6O$. The final anisotropic full-matrix least-squares refinement on $F^2$ with 255 variables converged at R1=4.27%, for the observed data and wR2=10.80% for all data. The goodness-of-fit is 1.066. The largest peak in the final difference electron density synthesis is 0.295 e⁻/Å³ and the largest hole is −0.204 e⁻/Å³ with an RMS deviation of 0.056 e⁻/Å³. On the basis of the final model, the calculated density is 1.376 g/cm³ and F(000), 872 e⁻. The absolute structure parameter is refined to 0.0(0), indicating the absolute structure of the molecule is consistent with the title compound. The acetonitrile solvent molecule is somewhat disordered and accordingly is refined isotropically, whereas (3R)-3-(5-fluoropyrimidin-4-yl)-3-methyl-6-(1H-pyrazol-4-yl)isoindolin-1-one and the chloride ions are refined anisotropically. This result for Example 5 establishes the absolute stereochemistry of the molecule as being the R enantiomer, thereby also establishing the stereochemistry of Example 3, from which Example 5 is derived.

Additionally, Examples 2 and 3 are subjected to analysis via chiral HPLC supercritical fluid chromatography (SFC) using the same conditions in order to determine the enantiomer present for each Example. (Column: Chiralcel OJ-H 4.6 mm×150 mm, 20% isopropanol in $CO_2$, 5 mL/min, UV 225 nm). For Example 2 and Example 3, Isomer 1 elutes at 1.53° and Isomer 2 elutes at 1.81-1.84°. In this analysis, Example 2 has 100% ee and Example 3 has 96.4% ee. These results demonstrate that the enantiomer present for both Example 2 and Example 3 is Isomer 2. Since the absolute stereochemistry for Example 3 is the R enantiomer, as provided above, and Examples 2 and 3 are both identified as by chiral HPLC SFC as Isomer 2, the absolute stereochemistry for Example 2 is, therefore, also the R enantiomer. Furthermore, since Example 2 is used to make Example 4, the absolute stereochemistry for Example 4 is the R enantiomer.

Acumen® Imaging Assay for Detection of Phosphorylated MCM2 in H1299 Cells

The Acumen® eX3 is used to determine the effect of compounds on the formation of endogenous phosphorylated MCM2 at Serine 53 (pMCM2-S53). Phosphorylation of MCM2 by CDC7 is determined using specific anti-pMCM2-S53 antibody and quantified with fluorescent tagged secondary antibodies by Acumen® eX3 to monitor CDC7 activity in cells. Phosphorylation of MCM2 at Serine 53 is known to be correlated to CDC7 inhibition.

H1299 cells (ATCC #CRL-5803) are maintained in RPMI-1640 (Hyclone SH30809.01) growth medium supplemented with 10% FBS. Cells are harvested using standard cell culture procedures and then counted using Vi-Cell XR Cell Viability Analyzer (Beckman Counter). 3000-6000 H1299 cells in 100 µL of growth medium are plated into each well of Biocoat Poly-D-Lysine 96-well black/clear plate with flat bottom Bio-Coat™ Multiwell (Becton Dickinson) cell culture plates 356640 and incubated overnight at 37° C., 5% $CO_2$.

Cells are treated with the test compound (50 µL/well) diluted in medium containing 0.6% DMSO and incubated for 4 hours at 37° C. To each well is added 7.4% formaldehyde (150 µL) diluted with PBS from 37% formaldehyde stock and the plates are incubated at room temperature for 30 minutes. Formaldehyde is removed and cold methanol (100 µL) is added. The plates are incubated for 20 minutes at 4° C. to permeabilize the cells. Plates are washed 3× with 100 µL/well of PBS. Plates are incubated with 50 µL/well of 1:1000 diluted anti pMCM2-S53 antibody (generated using NP_004517.2 (see PubMed Sequence Database), conjugation to keyhole limpet hemocyanin using maleimide activation, via standard 90-day rabbit immunization protocol for rabbit polyclonal antibody production (Thermo Scientific Pierce Antibodies, Thermo Fisher Scientific)) in PBS supplemented with 2% BSA overnight at 4° C. Plates are washed with PBS (4×100 µL/well) and incubated in 100 µL/well of 1:1000 diluted goat anti-rabbit IgG Alexa Fluor 488 secondary antibody (Invitrogen CA11304s) in PBS for 1 hour at room temperature. The plates are washed with PBS (4×100 µL/well). PBS (50 µL/well) containing RNase (50 µg/ml) and propidium iodide (15 µM) are added and the plates are incubated at room temperature for 30 minutes. The plates are sealed with black seal and are read on the Acumen® eX3 (TTP LABTECH) using optical filter 500-530 nanometer and 575-640 nanometer for Alexa Fluor 488 and propidium iodide, respectively. The number of pMCM2-S53 positive cells is normalized to total cells for each well and are calculated as percent inhibition relative to on-plate controls. The percent inhibition from the ten-point compound concentration data to a four parameter logistic equation is generated to derive the $IC_{50}$ value.

Compounds within the scope of the invention are tested in this assay substantially as described above. The compound of Example 2 is determined to have an $IC_{50}$ of 0.261 µM±0.004 (n=2). The compound of Example 3 is determined to have an $IC_{50}$ of 0.29 µM. The compound of Example 4 is determined to have an $IC_{50}$ of 0.29 µM+0.0813 (n=2). These results show that Examples 2, 3 and 4 inhibit pMCM2-S53 in the H1299 cell assay and thus are CDC7 inhibitors.

CDC7/DBF4 In Vitro Enzyme Assay

The Transcreener™ Kinase ADP-FP assay is used to determine compound $IC_{50}$ values against CDC7/DBF4 kinase. The Kinase ADP-FP assay assesses the activity of CDC7/DBF4 in the presence of compound inhibitors by measuring the concentration of ADP formed in a kinase reaction. The kinase reaction is performed using a 25 microliter reaction volume in 96 well assay plate. For the ADP-FP assay, the reagents are added to obtain the final reaction conditions of HEPES (25 mM) pH 7.5, 0.03% Triton® X-100, magnesium chloride (10 mM), DTT (1 mM), MCM2 (400 nM) (Amino Acid 1-209, a physiological substrate of CDC7/DBF4), spermine (4 mM), CDC7/DBF4 (2,640 ng/mL) (recombinant human CDC7/DBF4 expressed in insect cells), 4% dimethyl sulfoxide and serial dilutions of compound (diluted 1:3 from 20,000 nM to 1 nM). Enzyme and substrate is added to compound followed by ATP to 5 µM to start the reaction. The plates are incubated at room temperature for 60 minutes.

For the ADP-FP format add 25 microliters of a quench detection reagent containing HEPES (52 mM) pH 7.5, EDTA (20 mM), sodium chloride (0.4 M), polyoxyethyleneglycol dodecyl ether (0.02%) (BRIJ-35™), anti-ADP antibody (10 µg/mL), and ADP (4 nM) Transcreener® ADP Alexa Fluor® 633 tracer to quench the reaction. The plates are incubated for 1 hour, and then read in a Wallac EnVision™ 2104 Multilabel Reader (PerkinElmer) in Fluorescence Polarization mode using polarizing filters of $Ex_{620nm}$ and $Em_{688nm}$ wavelength. Millipolarization (mP) raw data is converted to micromolar ADP using a prepared ADP/ATP standard curve starting at 5 µM ADP 1:1 serial dilution in reaction buffer to 0.0025 µM ADP. The $IC_{50}$ value for each compound is derived using percent inhibition data calculated from the µM ADP reaction data relative to on-plate controls (DMSO versus 100 mM EDTA inhibited enzyme controls). The percent inhibition and ten-point compound concentration data is then fitted to a four-parameter logistic equation.

Compounds within the scope of the invention are tested in this assay substantially as described above. The compound of Example 2 is determined to have an $IC_{50}$ of 3.7 nM. The compound of Example 3 is determined to have an $IC_{50}$ of 4.5 nM. The compound of Example 4 is determined to have an $IC_{50}$ of 3.3 nM±0.634 (n=2). The results show that Examples 2, 3 and 4 inhibit ADP production in the in vitro enzyme assay and thus are CDC7 inhibitors.

In Vitro Antiproliferative Assay

In vitro anti-proliferative activity of Example 2 is determined by cell number counting assays against a panel of 114 cancer cell lines of colorectal, breast, lung, and blood (leukemia) origin obtained from ATCC, HSRRB, RIKEN or ECACC. The cells are cultured and maintained in media per supplier's instructions. Cell doubling time of each cell line is determined and all cell lines are free of mycoplasma contamination. Cells are cultured overnight in 96-well plates before compound addition for anti-proliferative activity assays. Optimal cell seeding density is carefully evaluated for each cell lines by seeding the cell culture with 4 different cell densities in 100 μL media and taking into consideration of their doubling time and cell sizes. The seeding density that gave about 90% confluence at end of two doubling times is then selected for compound testing. Staurosporine is used with 1:3 dilution as a reference. Example 2 is prepared as a 4 mM DMSO stock and diluted in culture media in a 1:2 ratio. 50 μL of the media containing the compound is added to each well of the overnight 96-well culture to produce the desired final concentrations of 20, 10, 5, 2.5, 1.25, 0.625, 0.312, 0.156, 0.078 μM and DMSO control. Each treatment concentration has duplicate wells. The cells are further cultured for two doubling times in the presence of the compound. At end of treatment time, cells are first examined under a microscope for morphological changes, such as cell death or apparent cell size increases. Cells in each duplicate well are collected separately. Adherent cells are harvested by tripsinization first. Harvested cells are re-suspended in growth media and are counted using a cell counter.

A compound within the scope of the invention is tested in this assay substantially as described above. As provided in Table 2 below, the compound of Example 2 demonstrates significant anti-proliferative activity against the majority of the 114 cancer cell lines tested at pharmacologically relevant concentrations (<8 μM). Furthermore, about 10% of the cancer cell lines show particular sensitivity to the compound, as demonstrated by massive cell death occurring for these cancer cells within 2 doubling time treatment periods. Most of these particularly sensitive cancer cell lines are derived from colorectal and leukemic cancers. The sensitivity is further confirmed in vivo in xenograft tumor models, such as Colo-205 and SW620 (see details below). This data demonstrates that Example 2 has broad antiproliferative activity in vitro in the cell lines tested.

TABLE 2

Broad in vitro anticancer activity of the compound of Example 2

| Cancer Cell Lines | Number of Cell Lines | Number of cell lines ($IC_{50}$ < 8 μM) | Number of cell lines ($IC_{50}$ > 8 μM) | Number of Cell Lines that Die Rapidly |
| --- | --- | --- | --- | --- |
| Colorectal | 29 | 18 | 11 | 4 |
| Lung | 39 | 29 | 10 | 2 |
| Breast | 17 | 10 | 7 | 0 |
| Leukemia | 23 | 18 | 5 | 5 |
| Others | 6 | 4 | 2 | 1 |
| Total | 114 | 79 | 35 | 12 |

CDC7 In Vivo Target Inhibition (IVTI) on MCM2-S40/41 Phosphorylation (pMCM2-S40/41) with Colo-205 Xenograft Tumor Model Human colo-205 colorectal cancer cells (ATCC#CCL-222) are maintained in RPMI 1640 medium containing 10% FBS. Log phase growing cells are harvested, washed, and resuspended in a 1:1 mixture of serum free medium and Matrigel™ (Becton Dickinson). They are injected subcutaneously at 5×10⁶ cells/animal/site in the rear flank as subcutaneous tumor xenograft models in balb/c (nu/nu) female mice (6-8 weeks with body weight of 20 to 25 gram/mouse). Animals are randomized at the mean tumor volume of 150 to 250 mm³ mice, (v=1×w×0.536 where 1=larger of measured diameter and w=smaller of perpendicular diameter). Compound is administered by P.O. in a standard 1% HEC w/v, P80 0.25% v/v, Antifoam 1510-US 0.05% v/v formulation. Tumors are harvested 4 hours post-dosing and disrupted by homogenization in lysis buffer (Invitrogen) containing protease inhibitor (Roche) and phosphatase inhibitor (Roche or Sigma). Protein concentration from tumor lysates is determined by BCA assay (Thermo Scientific) and 5 to 10 μg of protein is separated by standard SDS-PAGE (BioRad Criterion™ gel) or (Invitrogen ePage™ gel). Proteins are then transferred to PVDF or Nitrocellulose membrane and probed with antibodies against pMCM2-S40/41 (Bethyl Laboratories #A300-788A) or GAPDH (Fitzgerald 10R-G109A or Abcam ab9485) according to manufacturer and standard western blot protocol. Levels of pMCM2-S40/41 are determined and quantified by either Licor or FUJI imagers and normalized to the total GAPDH level. The percent change inhibition of pMCM2-S40/41 band intensity is calculated using the average intensity of vehicle treated control tumors normalized to the GAPDH as the maximum signal. The following formula is used to calculate the percent inhibition of signal in the treated tumor groups: Percent Inhibition=(normalized data−normalized max)/(zero−normalized max)*100. The $TED_{70}$ value relates the precise dose of the compound necessary to inhibit at 70% the average CDC7/DBF4-mediated phosphorylation of pMCM2 normalized to GAPDH (% target inhibition) in an in vivo xenograft experiment at 4 hours following an oral dose. The $TEC_{70}$ relates the precise plasma concentration of the compound necessary to inhibit at 70% the average CDC7/DBF4-mediated phosphorylation of pMCM2 normalized to GAPDH (% target inhibition) in an in vivo xenograft experiment at 4 hours following an oral dose.

A compound within the scope of the invention is tested in this assay substantially as described above. The $TED_{70}$ is generated from a plot of dose and % inhibition of pMCM2 and for Example 3 is 2.6 mg/kg. The $TEC_{70}$ is generated using the dose, % inhibition of pMCM2 and plasma concentration at 70% inhibition. The $TEC_{70}$ for Example 3 is 1.8 μM. This data demonstrates that a compound within the scope of the present invention inhibits the CDC7/DBF4-mediated phosphorylation of pMCM2 in a mouse in vivo xenograft experiment at 4 hours following an oral dose in mice.

Antitumor Efficacy in Human Colorectal Carcinoma SW620 Mouse Xenograft Model

The in vivo anticancer activity of Example 4 is studied in human colorectal adenocarcinoma cell line SW620 mouse xenograft tumor model which is predicted to be sensitive based on in vitro cell counting proliferative assay data described above. The SW620 cell line is obtained from American Type Culture Collection (ATCC) and is cultured in Leibovitz's L-15 Medium with 10% fetal bovine serum following ATCC instructions. SW620 cell suspension (5.0×10⁶/0.2 mL) is injected subcutaneously to the right flank of each female athymic Balb/c nude mice. The mice (5-6 weeks old at arrival) are obtained from Shanghai Sippr-bk Laboratory Animals Ltd. Upon receipt and throughout the study, the animals are housed 5 animals per cage in appropriately sized solid-bottom cages with contact bedding Animals are acclimated for 7 days prior to implantation of the SW620 cells. Animals are fed with Shanghai Laboratory Animal Center certified Rodent Diet with 23% Protein ad libitum and autoclaved tap water is provided ad libitum. The animal room is maintained on a 12-hour light/dark cycle. When the tumor volume reaches an average of 154.9 mm$^3$ (9 days post tumor implantation), the tumor bearing animals are randomly grouped into 9 groups (8 animals/group) with similar mean tumor volume and body weight. The average body weight of the tumor-bearing mice is 17.3 g. The compound is formulated in HEC 1% w/v, P80 0.25% v/v, and antifoam 1520-US 0.025% v/v in deionized water by probe sonication for 15 minutes on ice and compound formulation is prepared daily for animal dosing. The formulated compound is administered at 10.4, 20.8 and 31.2 mg/kg doses (containing 10, 20 and 30 mg/kg active pharmaceutical ingredient API, respectively) twice a day (BID) by oral gavage (0.1 mL/20 g) for 2 weeks. The BID dosing is performed about 8 hours apart (approximately 9 am and 5 pm each day). The vehicle is also given BID as the control arm of the study. Tumor volume and body weight are measured 3 times a week in a blinded manner. Tumor volume is determined by caliper measurements (mm) and using the formula for an ellipsoid sphere: tumor volume (mm$^3$)=length×width$^2$/2, where length and width refer to the larger and smaller perpendicular dimensions collected at each measurement. The animal behavior and animal health are monitored twice a day during dosing period. The study is terminated on day 28 post treatment initiation.

The statistical analysis of the tumor volume data begins with a data transformation to a log scale to equalize variance across time and treatment groups. The log volume data are analyzed with a two-way repeated measures analysis of variance by time and treatment using the MIXED procedures in SAS software (Version 9.3). The correlation model for the repeated measures is Spatial Power. Treated groups are compared to the control group at each time point. The MIXED procedure is also used separately for each treatment group to calculate adjusted means and standard errors at each time point. Both analyses account for the autocorrelation within each animal and the loss of data that occurs when animals with large tumors are removed from the study early. The adjusted means and standard errors are plotted for each treatment group versus time. The analysis comparing the treated groups to the control groups at each time point uses the log 10 tumor volumes and produces the p-values. For statistical significance of p-values shown, "***"=P<0.001.

If T>T0, the Delta T/C, % calculation is used. If T<T0 the Regression, % calculation is used:

Equations:
T=Final tumor volume in treated group
T0=Baseline tumor volume in treated group (assumed to be same as C0)
C=Final tumor volume in control group
C0=Baseline tumor volume in control group (assumed to be same as T0)

$$\text{Delta } T/C, \% = 100*(T-T0)/(C-C0)$$

$$\text{Regression}, \% = 100*(T-T0)/T0$$

TABLE 3

Dose dependent antitumor activity in SW620 mouse xenograft tumor model

| Group | Compound | Treatment (BID × 14, orally) | % T/C day 16 |
|---|---|---|---|
| 1 | Vehicle | | |
| 2 | Example 4 | 31.2 mg/kg | −66.1*** |
| 3 | Example 4 | 20.8 mg/kg | 5.7*** |
| 4 | Example 4 | 10.4 mg/kg | 26.1*** |

A compound within the scope of the invention is tested in this assay substantially as described above. As provided in Table 3 above, the compound of Example 4 demonstrates in vivo anticancer activity on the SW620 xenograft tumors in a dose-dependent manner when given BID continuously for 2 weeks. The results for all doses tested are significantly smaller than for the vehicle. This activity is consistent with the in vitro activity observed with SW620 cancer cell line. At the maximum tolerated dose of 31.2 mg/kg, the compound causes significant tumor regression, as shown by the negative value. Also, no significant tumor growth is observed for 2 weeks after dosing cessation. This data demonstrates that Example 4 provides dose dependent antitumor activity in a SW620 mouse xenograft tumor model.

We claim:

1. A compound which is 3-(5-fluoropyrimidin-4-yl)-3-methyl-6-(1H-pyrazol-4-yl)isoindolin-1-one, or a pharmaceutically acceptable salt or hydrate thereof.

2. The compound according to claim 1 which is 3-(5-fluoropyrimidin-4-yl)-3-methyl-6-(1H-pyrazol-4-yl)isoindolin-1-one.

3. The compound according to claim 1, which is 3-(5-fluoropyrimidin-4-yl)-3-methyl-6-(1H-pyrazol-4-yl)isoindolin-1-one, isomer 2, or a pharmaceutically acceptable salt thereof.

4. The compound according to claim 3, which is 3-(5-fluoropyrimidin-4-yl)-3-methyl-6-(1H-pyrazol-4-yl)isoindolin-1-one, isomer 2.

5. The compound according to claim 1, which is 3-(5-fluoropyrimidin-4-yl)-3-methyl-6-(1H-pyrazol-4-yl)isoindolin-1-one, isomer 1, or a pharmaceutically acceptable salt thereof.

6. The compound according to claim 5, which is 3-(5-fluoropyrimidin-4-yl)-3-methyl-6-(1H-pyrazol-4-yl)isoindolin-1-one, isomer 1.

7. The compound according to claim 1 which is 3-(5-fluoropyrimidin-4-yl)-3-methyl-6-(1H-pyrazol-4-yl)isoindolin-1-one, or hydrate thereof.

8. The compound according to claim 7 which is a hydrate in a crystalline form characterized by a X-ray powder diffraction pattern having characteristic peaks, in 2θ±0.2, occurring at 22.27 and one or more of 13.46, 16.54, 16.66, 18.10 and 23.13.

9. A pharmaceutical composition comprising a compound which is 3-(5-fluoropyrimidin-4-yl)-3-methyl-6-(1H-pyrazol-4-yl)isoindolin-1-one, or a pharmaceutically acceptable salt or hydrate thereof, and a pharmaceutically acceptable carrier, diluent, or excipient.

10. The pharmaceutical composition according to claim 9 comprising the compound which is 3-(5-fluoropyrimidin-4-yl)-3-methyl-6-(1H-pyrazol-4-yl)isoindolin-1-one.

11. The pharmaceutical composition according to claim 9 comprising the compound which is 3-(5-fluoropyrimidin-4-yl)-3-methyl-6-(1H-pyrazol-4-yl)isoindolin-1-one, isomer 2, or a pharmaceutically acceptable salt thereof.

12. The pharmaceutical composition according to claim 11 comprising the compound which is 3-(5-fluoropyrimidin-4-yl)-3-methyl-6-(1H-pyrazol-4-yl)isoindolin-1-one, isomer 2.

13. The pharmaceutical composition according to claim 9 comprising the compound which is 3-(5-fluoropyrimidin-4-yl)-3-methyl-6-(1H-pyrazol-4-yl)isoindolin-1-one, isomer 1, or a pharmaceutically acceptable salt thereof.

14. The pharmaceutical composition according to claim 13 comprising the compound which is 3-(5-fluoropyrimidin-4-yl)-3-methyl-6-(1H-pyrazol-4-yl)isoindolin-1-one, isomer 1.

15. The pharmaceutical composition according to claim 9 comprising the compound which is 3-(5-fluoropyrimidin-4-yl)-3-methyl-6-(1H-pyrazol-4-yl)isoindolin-1-one, or hydrate thereof.

16. The pharmaceutical composition according to claim 15 comprising the compound which is a hydrate in a crystalline form characterized by a X-ray powder diffraction pattern having characteristic peaks, in 2θ±0.2, occurring at 22.27 and one or more of 13.46, 16.54, 16.66, 18.10 and 23.13.

17. A method of treating a cancer wherein the cancer is selected from the group consisting of breast cancer, lung cancer, colorectal cancer, and leukemia, comprising administering to a patient in need thereof, an effective amount of a compound which is 3-(5-fluoropyrimidin-4-yl)-3-methyl-6-(1H-pyrazol-4-yl)isoindolin-1-one, or a pharmaceutically acceptable salt or hydrate thereof.

18. The method according to claim 17 comprising the compound which is 3-(5-fluoropyrimidin-4-yl)-3-methyl-6-(1H-pyrazol-4-yl)isoindolin-1-one.

19. The method according to claim 17 comprising the compound which is 3-(5-fluoropyrimidin-4-yl)-3-methyl-6-(1H-pyrazol-4-yl)isoindolin-1-one, isomer 2, or a pharmaceutically acceptable salt thereof.

20. The method according to claim 19 comprising the compound which is 3-(5-fluoropyrimidin-4-yl)-3-methyl-6-(1H-pyrazol-4-yl)isoindolin-1-one, isomer 2.

21. The method according to claim 17 comprising the compound which is 3-(5-fluoropyrimidin-4-yl)-3-methyl-6-(1H-pyrazol-4-yl)isoindolin-1-one, isomer 1, or a pharmaceutically acceptable salt thereof.

22. The method according to claim 21 comprising the compound which is 3-(5-fluoropyrimidin-4-yl)-3-methyl-6-(1H-pyrazol-4-yl)isoindolin-1-one, isomer 1.

23. The method according to claim 17 comprising the compound 3-(5-fluoropyrimidin-4-yl)-3-methyl-6-(1H-pyrazol-4-yl)isoindolin-1-one, or hydrate thereof.

24. The method according to claim 23 comprising the compound which is a hydrate in a crystalline form characterized by a X-ray powder diffraction pattern having characteristic peaks, in 2θ±0.2, occurring at 22.27 and one or more of 13.46, 16.54, 16.66, 18.10 and 23.13.

25. The method according to claim 17, wherein the cancer is colorectal cancer.

26. The method according to claim 18, wherein the cancer is colorectal cancer.

27. The method according to claim 19, wherein the cancer is colorectal cancer.

28. The method according to claim 20, wherein the cancer is colorectal cancer.

29. The method according to claim 21, wherein the cancer is colorectal cancer.

30. The method according to claim 22, wherein the cancer is colorectal cancer.

31. The method according to claim 23, wherein the cancer is colorectal cancer.

32. The method according to claim 24, wherein the cancer is colorectal cancer.

* * * * *